(12) United States Patent
Fitzgibbons et al.

(10) Patent No.: US 6,773,417 B2
(45) Date of Patent: Aug. 10, 2004

(54) EPIDURAL SPACE LOCATING DEVICE

(75) Inventors: James F. Fitzgibbons, Bantam, CT (US); Christopher S. Young, South Kent, CT (US)

(73) Assignee: ISPG, Inc., New Milford, CT (US)

( * ) Notice: Subject to any disclaimer, the term of this patent is extended or adjusted under 35 U.S.C. 154(b) by 412 days.

(21) Appl. No.: 09/900,219

(22) Filed: Jul. 6, 2001

(65) Prior Publication Data

US 2003/0009135 A1 Jan. 9, 2003

(51) Int. Cl.[7] ............................................... A61M 5/00
(52) U.S. Cl. ..................................... 604/118; 604/117
(58) Field of Search ................................ 604/117, 118, 604/216, 217, 75; 606/1

(56) References Cited

U.S. PATENT DOCUMENTS

| | | | |
|---|---|---|---|
| 3,583,387 A | | 6/1971 | Garner et al. |
| 3,796,542 A | | 3/1974 | Kline |
| 4,801,293 A | * | 1/1989 | Jackson ....................... 604/505 |
| 5,492,304 A | | 2/1996 | Smith et al. |
| 5,685,852 A | * | 11/1997 | Turkel et al. ................ 604/159 |
| 5,695,474 A | * | 12/1997 | Daugherty ................... 604/162 |
| 5,725,509 A | * | 3/1998 | Scarfone et al. ............ 604/217 |
| 5,902,273 A | | 5/1999 | Yang et al. |

* cited by examiner

*Primary Examiner*—Manuel Mendez
(74) *Attorney, Agent, or Firm*—Carmody & Torrance LLP

(57) ABSTRACT

An epidural space locating device for locating an epidural space, the device comprising a body section having a first end and a second end and a longitudinal passageway extending therethrough, the first end of which is coupleable to a luer assembly; and a collapsible bellows chamber having one end coupled to the second end of the body section and the other end exposed so as to permit pressure to be exerted thereon by one or more digits of a hand, wherein positive pressure within the bellows chamber maintains the integrity of the shape of the bellows chamber and wherein negative or zero pressure within the bellows chamber facilitates the collapsing of the shape of the bellows chamber thus indicating the locating of the epidural space by a needle that is coupled to the luer assembly; wherein the loss of pressure within the bellows chamber is sensed by the one or more digits of the hand as the shape of the bellows chamber collapses.

23 Claims, 4 Drawing Sheets

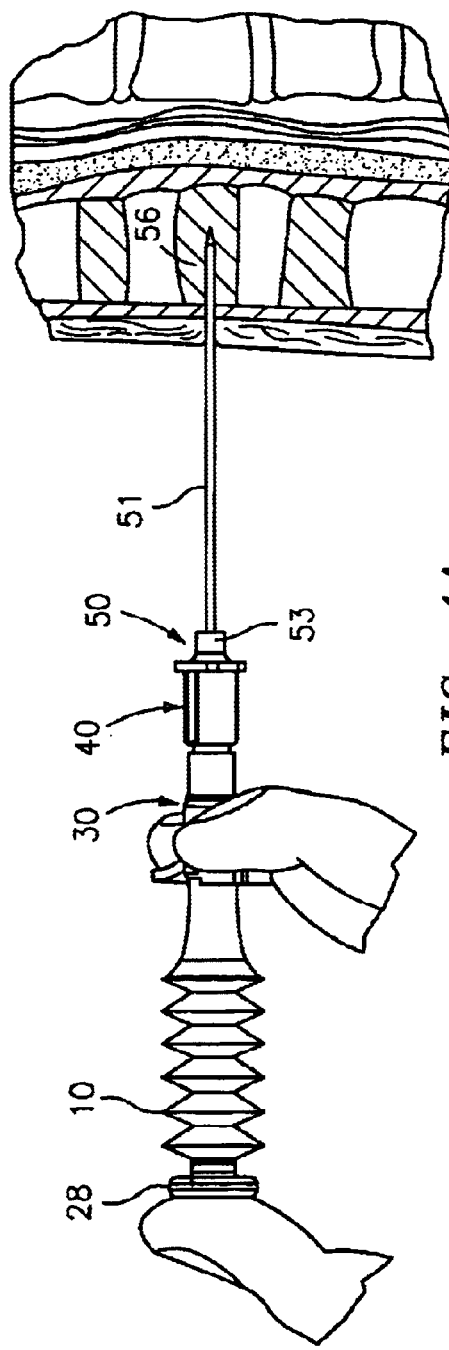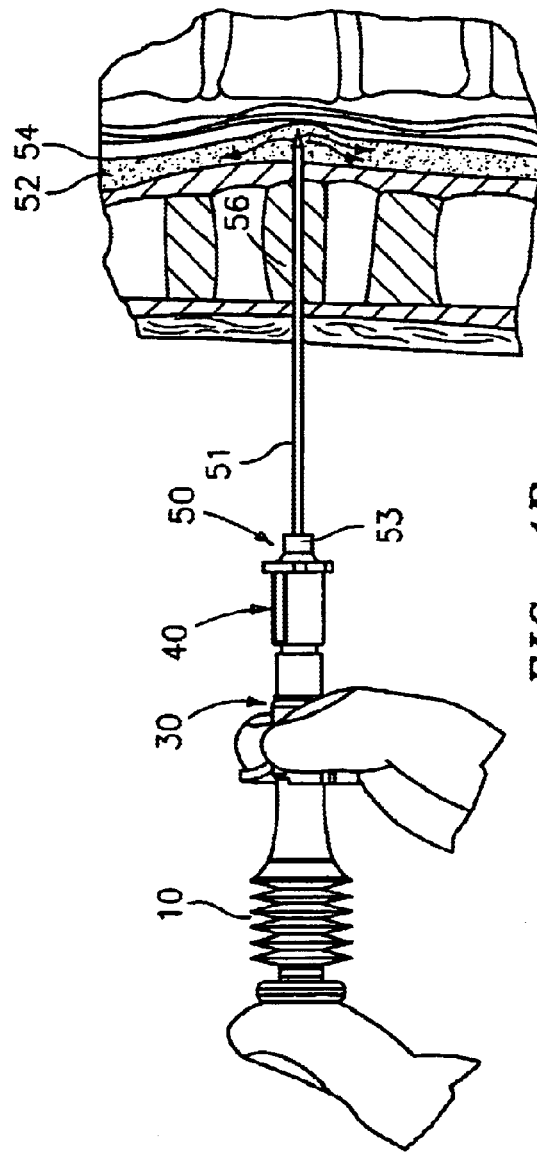
FIG. 4A
FIG. 4B

EPIDURAL SPACE LOCATING DEVICE

BACKGROUND OF THE INVENTION

The present invention relates to an epidural space locating device for detecting the epidural space while protecting the dura mater in the spinal column of humans. In particular, the present invention relates to a spinal epidural space locating device that maintains positive pressure within a bellows chamber until the epidural space is located, and at which time zero or negative pressure more easily permits the collapsing of the bellows chamber of the epidural space locating device. In accordance with the present invention, this change of pressure is preferably sensed by a visual collapsing of the bellows chamber and/or reduction of pressure against a thumb of the hand operating the epidural space locating device. Methods of using such an epidural space locating devices are also provided.

As is well known, to avoid the side-effects of drugs on the brain, analgesic or anesthetic drugs can be delivered to the spinal cord by placing the drugs outside of the membranous sac containing the spinal cord. Between this sac, called the dura, and the overlying spinal ligaments, is a space called the spinal epidural space. Placing drugs in the spinal epidural space blocks spinal cord functions including pain transmission.

In practice, locating the spinal epidural space with a needle requires great care because it is difficult to sense the change in resistance as the needle passes through the spinal ligaments. It is desirable to reach the epidural space and stop before going through the dura. The concern, and therefore risk in the procedure, is the undesirable puncture of the dura. Identification of the precise moment when the needle is advanced into the epidural space is thus very desirable.

Present methods for identifying this space fall into two main categories: the "loss of resistance" and the "hanging drop" techniques. The "loss of resistance" method is the most commonly used technique to identify the spinal epidural space. The "loss of resistance" technique involves direction of the epidural needle through the skin into the interspinous ligament. One example of a device that utilizes the "loss of resistance" technique is described in U.S. Pat. No. 5,902,273 to Yang et al. Yang et al describe a combination of a pressure chamber, syringe to build up pressure within the pressure chamber, and indicator section with a corresponding pressure indicator bar to indicate a loss of pressure within the pressure chamber. Specifically, Yang et al describe a device and method whereby a one-way valve for positive pressure build-up and an attached pressure indicator identifies the loss of positive pressure when the needle enters the epidural space. In particular, when the plunger is pulled outwardly, air will be drawn to the syringe housing, and when the plunger is thereafter pushed inwardly, air will be pushed into the pressure chamber through the one-way valve. When the epidural needle reaches the epidural space, the positively pressurized air will deflect the dura mater away from the needle tip as it escapes from the chamber, through the needle, and into the epidural space. The positive pressure in the chamber will drop immediately, and an indicator will return to its original position due to a corresponding spring force.

Other less intricately constructed devices are also well known. For example, another commonly used device is the free sliding glass syringes, or with improved plastic materials, a more or less free sliding plastic syringe. In these examples, when the needle tip is properly positioned within the substance of the interspinous ligament, depression of the syringe plunger by a thumb will not be possible. As the needle is advanced, the injecting hand is placed on the plunger of the syringe with continuous pressure. As the needle passes through the ligamentum flavum and enters the epidural space, a sudden loss of resistance within the syringe occurs and this change of pressure can be sensed by the ease by which the plunger is slideable within the syringe. The medication can then be injected into the epidural space in a known manner.

It is perceived that the construction of the epidural space locating device described by Yang et al is unduly complicated. Moreover, there are several disadvantages in using aforementioned free-sliding glass or plastic syringes. In particular, extreme experience is needed to maintain the required alignment between the plunger and the longitudinal bore of the syringe. Inadvertent and thus undesirable angling of the plunger against the inner side walls of the syringe results in friction therebetween and possibly hindering the ability to recognize, precisely locate and time the locating of the epidural space. While this problem is not as common with glass syringes, the problem is more pronounced and common with syringes made of plastic. While it would therefore appear that continued use of free-sliding glass syringes may be acceptable, it is well known that such syringes are undesirably expensive.

Therefore, it is desirable to provide an epidural space locating device that overcomes the foregoing perceived disadvantages and achieves the objectives set forth below.

SUMMARY AND OBJECTS OF THE INVENTION

It is therefore an object of the present invention to provide an improved epidural space locating device that overcomes the foregoing perceived deficiencies.

It is another object of the present invention to provide an improved epidural space locating device that more easily allows a user to locate the epidural space for epidural anesthesia or analgesia, among other things.

It is yet another object of the present invention to provide an epidural space locating device that has enough positive pressure to effectively deflect the dura mater upon entrance of the needle into the epidural space, thus effectively preventing dural puncture.

It is still a further object of the present invention to provide an epidural space locating device that can be made smaller and less cumbersome than prior art devices.

It is still another object of the present invention to provide a user with an improved epidural space locating device that provides for reliable needle advancing and epidural space locating.

Another object of the present invention is to provide the epidural space locating device operator with an immediate indication of "loss of positive pressure" for ease of use and training, and one that is more consistent with devices already known in the art.

An additional object is to provide an improved epidural space locating device that achieves all the advantages provided by a free-sliding glass syringe but which is significantly less costly to manufacture.

Still another objective of the present invention is to provide an improved epidural space locating device that does not require the precise alignment required by present known plungers and syringes.

And yet another objective of the present invention is to provide a locating device that utilizes a collapsible bellows within which a loss of resistance can be sensed or otherwise felt by the operator, such as by the operator's thumb thereby providing the operator with the desired "feel" that the operator was previously used to.

Yet another object of the present invention is to provide an epidural space locating device that can be filled with saline solution in another embodiment utilizing the "loss of resistance" technique.

Still another objective of the present invention is to provide methods of using an epidural space locating device constructed in accordance with the present invention.

Still other objects and advantages of the invention will in part be obvious and will in part be apparent from the specification.

The invention accordingly comprises the features of construction, combination of elements and arrangement of parts and sequence of steps which will be exemplified in the construction, illustration and description hereinafter set forth, and the scope of the invention will be indicated in the claims.

Generally speaking, in accordance with the present invention, an epidural space locating device for locating an epidural space, is provided. In one embodiment of the invention, the device may comprise a body section having a first end and a second end and a longitudinal passageway extending therethrough, the first end of which is coupleable to a luer assembly; and a collapsible bellows chamber having one end coupled to the second end of the body section and the other end exposed so as to permit pressure to be exerted thereon by one or more digits of a hand, wherein positive pressure within the bellows chamber maintains the integrity of the shape of the bellows chamber and wherein negative or zero pressure within the bellows chamber facilitates the collapsing of the shape of the bellows chamber thus indicating the locating of the epidural space by a needle that is coupled to the luer assembly as the needle enters the epidural space; wherein the loss of pressure within the bellows chamber is sensed by the one or more digits of the hand as the shape of the bellows chamber collapses.

The present invention may also incorporate a luer lock, coupled to the first end of the body section, for air-tightly coupling a needle to the body section and a needle assembly, comprising a needle hub and epidural needle, coupled to the luer lock. Preferably, the bellows chamber includes a neck portion, the neck portion being air-tightly coupled to the second end of the body section, and wherein the neck portion has an air passageway that is inline with the longitudinal passageway extending through the body section. In a particular embodiment, the bellows chamber and the neck portion may be integrally formed and the neck portion and the first end of the body section are threadably coupled. The first end of the bellows chamber may include a concave surface for supporting the thumb of the hand, wherein the negative or zero pressure within the bellows chamber is detected by the thumb of the hand as the bellow chamber collapses. In yet a particular configuration, the bellows chamber may be made of polyethylene or rubber, or other sufficiently flexible material.

In yet another embodiment of the present invention, a method for detecting the entry of a needle into the epidural space of a patient is provided. In this embodiment, the method may comprise the steps of providing an epidural space locating device comprising a body section having a first end and a second end and a longitudinal passageway extending therethrough, the first end of which is coupleable to a luer assembly; and a collapsible bellows chamber having a first end coupled to the second end of the body section and a second end exposed so as to permit pressure to be exerted thereon by one or more digits of a hand, wherein positive pressure within the bellows chamber maintains the integrity of the shape of the bellows chamber and wherein negative or zero pressure within the bellows chamber facilitates the collapsing of the shape of the bellows chamber thus indicating the locating of the epidural space by a needle that is coupled to the luer assembly; coupling a luer assembly and epidural needle to said locating device; inserting the needle into a patient towards the patient's epidural space; and continuing to insert the needle towards the patient's epidural space while applying pressure against the second end of the bellows chamber by a digit of a hand until the shape of the bellows chamber begins to collapse, thereby indicating entrance into the epidural space.

In this embodiment, the method may include the step of sensing a drop of pressure in the bellows chamber by the thumb of the hand which is against the second end of the bellows chamber. As would be understood, the method may include the step of inserting the needle into at least the interspinous ligament as the needle is moving towards the epidural space. In one preferred methodology, the invention would include the steps of introducing a solution, such as but not limited to saline, into the bellows chamber; inserting the needle into a patient towards the patient's epidural space; and continuing to insert the needle towards the patient's epidural space while applying pressure against the second end of the bellows chamber by a digit of a hand until the shape of the bellows chamber begins to collapse by the solution being introduced into the epidural space, thereby indicating entrance into the epidural space. Here, the solution may be introduced into the bellows chamber as the second end of the bellows chamber is pulled in a direction away from the body section.

Lastly, the present invention is directed to a method for deflecting a patient's dura for preventing dural puncture, in which the method comprises the steps of providing an epidural space locating device comprising a body section having a first end and a second end and a longitudinal passageway extending therethrough, the first end of which is coupleable to a luer assembly; and a collapsible bellows chamber having a first end coupled to the second end of the body section and a second end exposed so as to permit pressure to be exerted thereon by one or more digits of a hand, wherein positive pressure within the bellows chamber maintains the integrity of the shape of the bellows chamber and wherein negative or zero pressure within the bellows chamber facilitates the collapsing of the shape of the bellows chamber thus indicating the locating of the epidural space by a needle that is coupled to the luer assembly; coupling a luer assembly and epidural needle to said locating device; inserting the needle into a patient towards the patient's epidural space; and continuing to insert the needle towards the patient's epidural space while applying pressure against the second end of the bellows chamber by a digit of a hand until the shape of the bellows chamber begins to collapse, thereby deflecting a patient's dura for preventing dural puncture.

Similarly, the method may include the step of sensing a drop of pressure in the bellows chamber by a thumb of the hand against the second end of the bellows chamber and/or inserting the needle into at least the interspinous ligament as the needle is moving towards the epidural space. Likewise, the method in accordance with the present invention may include the steps of introducing a solution into the bellows chamber; inserting the needle into a patient towards the patient's epidural space; and continuing to insert the needle towards the patient's epidural space while applying pressure against the second end of the bellows chamber by a digit of a hand until the shape of the bellows chamber begins to collapse by the solution being introduced into the epidural space, thereby indicating entrance into the epidural space.

BRIEF DESCRIPTION OF THE DRAWINGS

For a fuller understanding of the invention, reference is had to the following description taken in connection with the accompanying figures, in which:

FIGS. 4A and 4B are illustrations showing the preferred manner of use of the present invention, with FIG. 4A particularly showing the initial steps of the present invention being inserted into the interspinous ligament while FIG. 4B particularly showing the present invention after the needle has just entered the epidural space and the deflection of the dura by the pressure of the air or saline, as the case may be, thereby achieving a successful location of the epidural space.

DETAILED DESCRIPTION OF THE PREFERRED EMBODIMENTS

Figure 1:
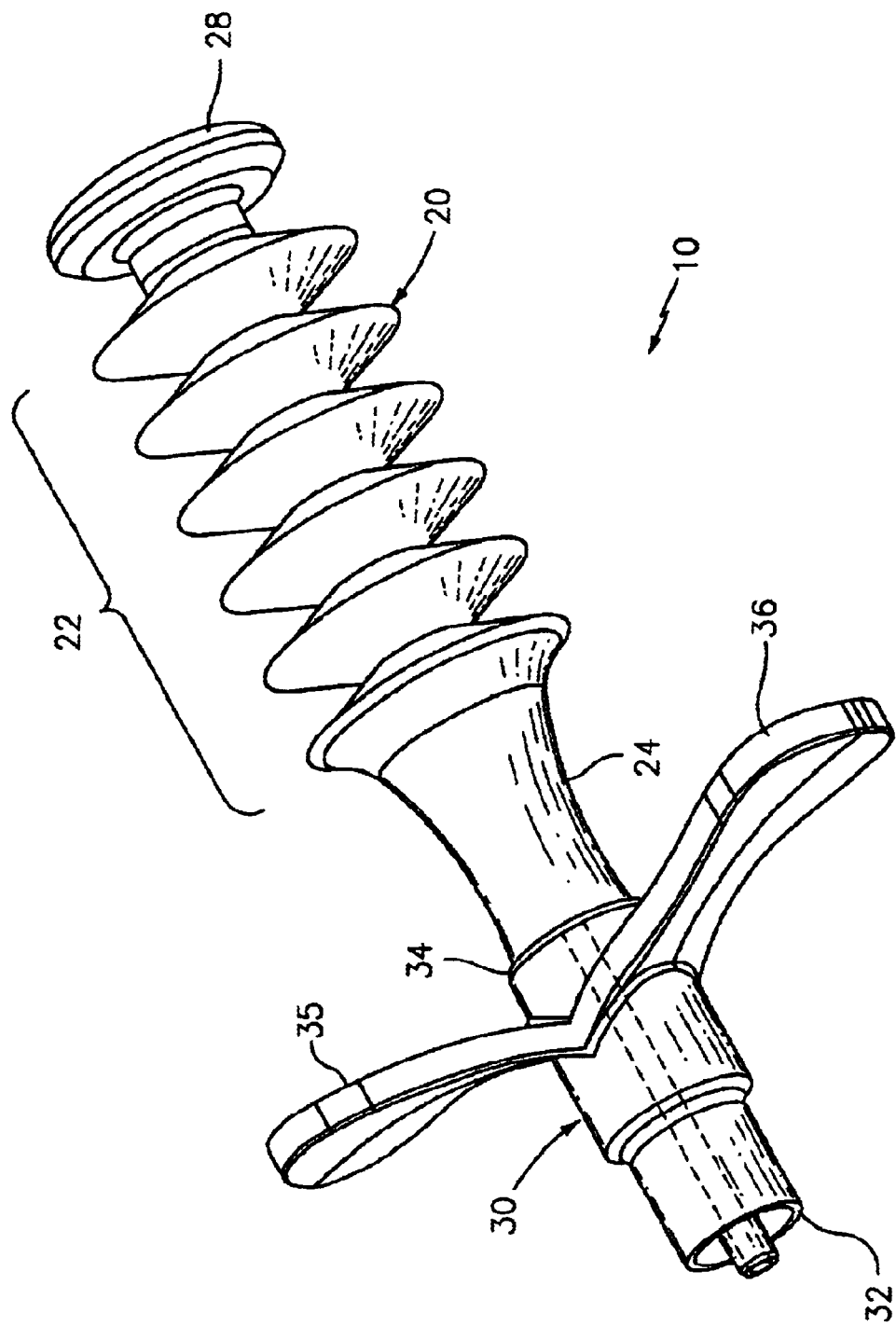
FIG. 1 is a perspective view of an epidural space locating device constructed in accordance with the present invention.
Figure 2:
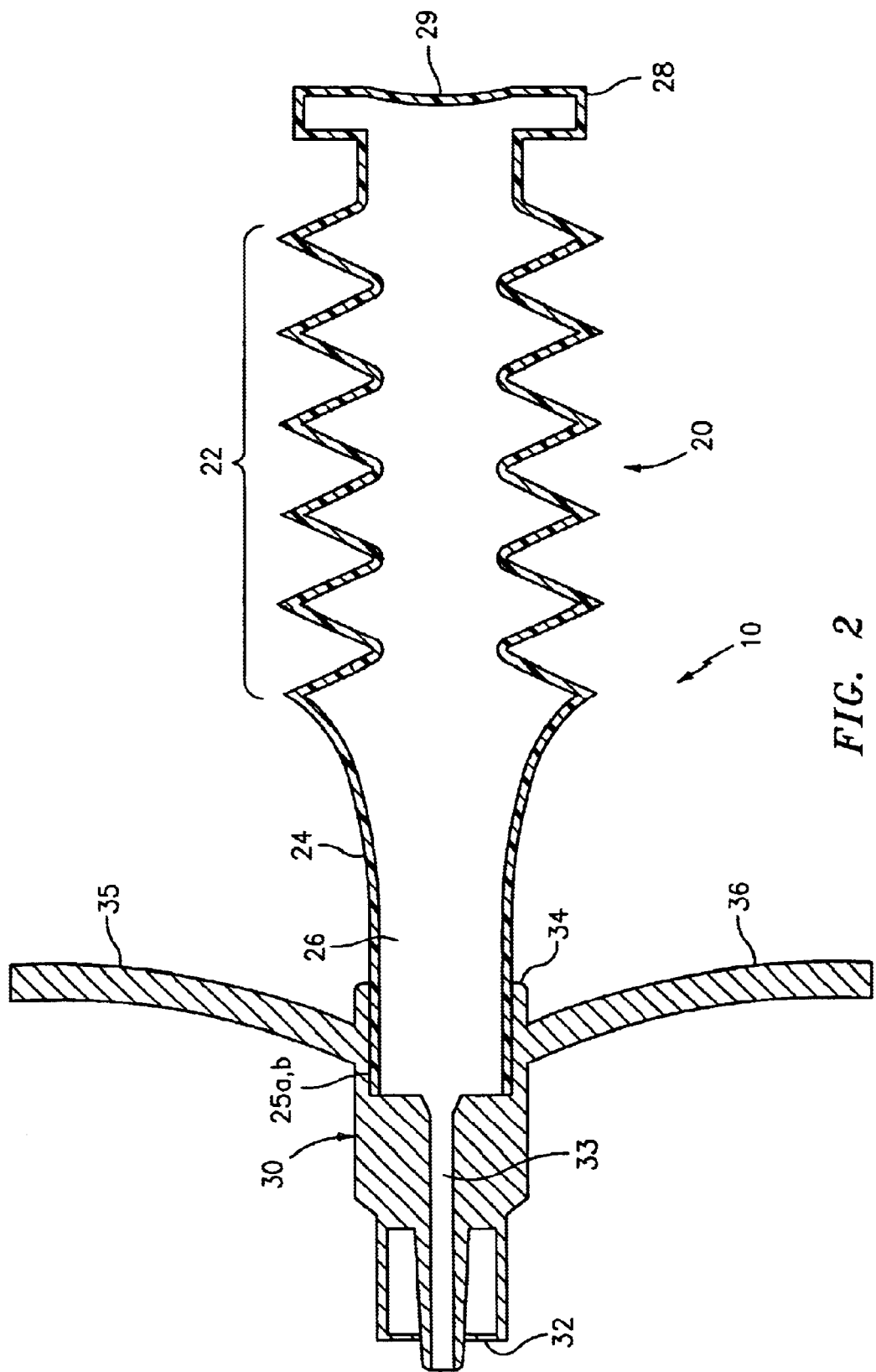
FIG. 2 is a cross-sectional view of the epidural space locating device illustrated in FIG. 1.
Figure 3:
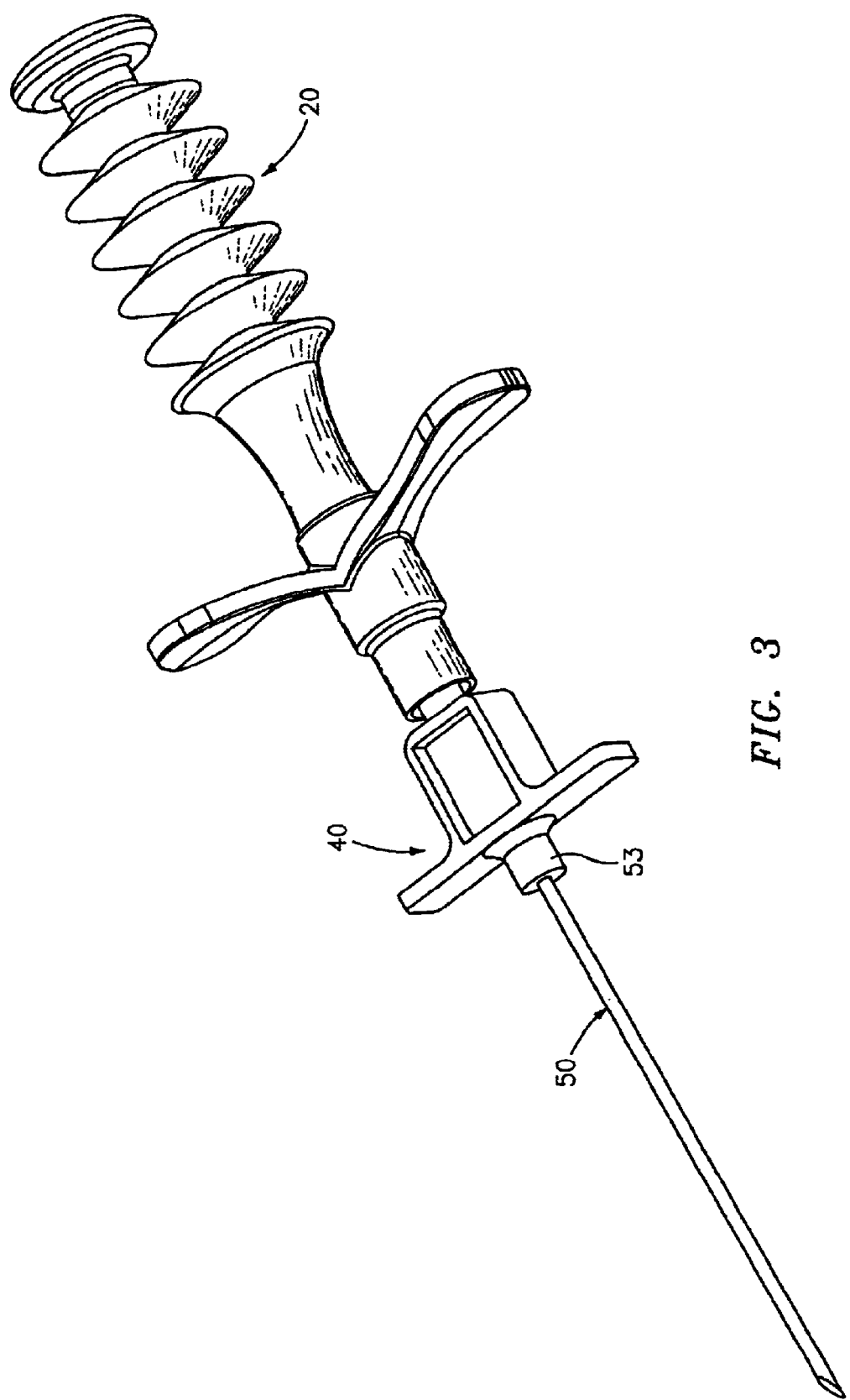
FIG. 3 is a perspective view of the epidural space locating device of FIG. 1 further illustrating a standardized luer lock locking device and needle.

Generally speaking, reference will be made to FIGS. 1–3, wherein an epidural space locating device (hereinafter the "locating device"), generally indicated at 10 and constructed in accordance with the present invention, is depicted.

Locating device 10, in its fully completed and operational configuration, preferably comprises four main components, namely a collapsible bellows chamber generally indicated at 20, a body section generally indicated at 30, a luer assembly 40, such as lock or slip as would be understood in the art (reference being made below to a luer lock by way of example and not limitation), and a needle assembly 50, which itself may include a needle hub and/or just an epidural needle as would be known in the art. The operable coupling and construction of the foregoing components and method of using locating device 10 will be now be discussed.

Body section 30 includes a first end 32 and a second end 34 and includes a longitudinal passageway 36 extending therethrough. First end 32 of body section 30 is air-tightly coupled to luer lock 40 in a manner that would be well understood in the art and in accordance with standards also well known by those skilled in the art. Similarly, needle assembly 50 is coupled to luer lock 40 in a known manner.

Bellows chamber 20 includes a collapsible portion 22 and a preferably integrally formed neck portion 24, one end of neck portion 24 being coupled to second end 34 of body section 30, preferably by a friction fit or the threading of an outer surface of neck portion 24 and a corresponding inner surface of second end 34 (corresponding threads 25a, b). Importantly, collapsible portion 22 of bellows chamber 20 is exposed to allow for human touch so as to permit pressure to be exerted thereon by one or more digits of an operator's hand, and in the preferred embodiment, an operator's thumb, as more particularly described below. For this purpose, an integrally formed end cap 28 is provided at the top of bellows chamber 20 and may have a concavely formed top surface 29 to facilitate the support of the operator's thumb.

The cap 28 may be easily grabbed by a user's fingers as explained below so as to facilitate the acceptance of the saline or air within collapsible portion 22.

As should now be clear, neck portion 24 has an air passageway 26 that is inline with longitudinal passageway 36 extending through body section 30.

Also provided on body section 30 are a pair of outwardly extending wings, or finger grips 35, 37. Finger grips 35, 37 may be integrally molded on, or snap-fitted or adhesively coupled to, an outer surface of body section 30 and, along with body section 30, may be formed of polycarbonate.

On the other hand, bellows chamber 20 is preferably formed of polyethylene or other extra thin material, such as certain types of rubber or silicone. Importantly, collapsible portion 22 must easily collapse upon the loss of resistance as discussed below. Materials to form luer lock 40 and needle assembly 50 are well known and the formation of these standard assemblies are also well known. In fact, the present invention, being primarily directed to the collapsible bellows chamber 20 in combination with body section 30, is intended to accommodate standardized luer locks and corresponding needle assemblies. Therefore, details directed thereto will be omitted herein for brevity.

Importantly, and in direct distinction to the construction proposed by Yang et al, the passageway created by the needle 51, needle hub 53, body section 30 and neck portion 24 of bellows chamber 20 are all inline. Normal atmospheric pressure may therefore be present in the collapsible portion 22 of bellows chamber 20 since air can flow through the tip of the needle into bellows chamber 20.

As illustrated in FIGS. 4A and 4B, in operation, needle assembly 50 is coupled to luer lock 40 which itself is coupled in a known manner to body section 30 of locating device 10. If the loss of resistance technique is used in connection with normal air pressure, then as stated above, bellows chamber 20 will be filled with air. However, in accordance with an alternate method of utilizing the present invention, the loss of resistance method could be used with locating device 10 after being filled with a solution, such as saline solution. That is, upon the completion of the coupling of the bellows chamber 20, body section 30, luer lock 40 and needle assembly 50, the user may fill chamber 20 with saline solution or other solutions of sufficient purity, by pulling cap 28 in a direction away from body section 30, in such a way as to replicate the "sucking" action of a plunger of a syringe. In this manner, the method of filling the bellows chamber with saline may be similar to the manner in which a syringe would be filled with saline. Alternatively, the saline solution may be added prior to the completed coupling of the needle assembly 50, luer lock 40, body section 30 and chamber 20.

The needle 51 may then be inserted into the interspinous ligament towards the epidural space. Locating device 10 is positively pressurized with air (or saline as the case may be) as the needle 51 is lodged in the interspinous ligament 56, and is pressurized to a level optimal for deflection of the dun 54. Thus pressurized, the epidural needle 51 is pushed by the hand of the operator (such as a doctor or other medical/authorized personnel) in a manner such that the operator's thumb is preferably placed in the concave top surface 29 of bellows chamber 20 while the operator's index and middle finger are placed against grips 35, 37, respectively. The needle 51 is pushed towards the epidural space 52 until there is a loss of positive pressure upon entrance of the needle into the epidural space 52. If the bellows chamber 20 is filled with air, the air may deflect the dura 54. If the bellows chamber is filled with saline, the release thereof into the epidural space 52 would also protect the dura in a known manner. Importantly, the bellows chamber 20 collapses very easily, and the moment a loss of resistance occurs, the collapsible portion 22 of chamber 20 begins to collapse. The use of the bellows chamber is therefore superior to the use of a syringe because the alignment of the plunger with respect to the syringe housing need not be maintained so critically. Bellows chamber 20 may then be disengaged from body section 30 by disconnecting needle assembly 50 from luer lock 40. In this way the appropriate anesthetic or analgesic administering device may be engaged to needle assembly 50 in order to administer the medication to the epidural space.

Importantly, the operator of locating device 10 can directly feel the positive pressure in bellows chamber 20 by his/her thumb on the top surface 29 of bellows chamber 20 as the epidural needle 51 is being lodged in the interspinous ligament since the air (or saline) inside bellows chamber 20 cannot escape through the tip of the needle 51. The thumb can best sense this positive pressure. It is for this reason that the bellows chamber is directly exposed to allow for human touch in direct contradiction of that described by Yang et al which completely encloses its indicator section. The air-tight arrangement of locating device 10 prevents air (or saline) from escaping and thereby prevents the occurrence of a false indication that the epidural space has been located when it hasn't been located. Sensitivity must be sufficient to ensure that the needle 51 has entered the epidural space rather than soft tissue.

Once the tip of the needle 51 has advanced through the interspinous ligament 56 and entered the epidural space 52, the lack of pressure on the tip of the needle creates a pressure gradient between bellows chamber 20 and the epidural space through the needle causing the air (or saline) compressed in bellow chamber 20 to rush into the epidural space 52. This in turn causes a collapsing of the collapsible portion 22 due to the gentle but sufficient pressure by the thumb on the surface 29 of bellows chamber 20. Deflection of the dura 54 occurs as the air (or saline) exits the tip of the needle and deflects the dura 54 away from the tip of the needle. The deflection of the dura will protect the dura from being punctured by the needle, thus increasing the safety of the procedure disclosed herein. Experience in sensing the change of pressure against the thumb in combination with the collapsing of the bellows chamber 20 quickly enables one to recognize that the needle has entered the epidural space. Also, as set forth above, sufficiently less exactness in maintaining a proper alignment between bellows chamber 20 and body section 30 needs to exist than that required by the plunger orientation in the glass or plastic syringes. That is, the negative or zero pressure and corresponding collapse of bellows chamber 20 will indicate the loss of positive pressure which signals entrance of needle into the epidural space. Further details of how the present invention may be effectively used are set forth in an article by Alice Gaynor, entitled "The Lumbar Epidural Region: Anatomy and Approach" as published in Epidural & Spine Blockade in Obstetrics, London: Bailliere Tindall, 1990 pp 12–15 and is hereby incorporated by reference as if fully set forth herein.

It will thus be seen that the objects set forth above, among those made apparent from the preceding description, are efficiently attained and, since certain changes may be made in the above constructions and methodologies without departing from the spirit and scope of the invention, it is intended that all matter contained in the above description or shown in the accompanying drawings shall be interpreted as illustrative and not in a limiting sense.

For example, the bellows chamber 20 may be directly coupled to the luer lock 40 thereby eliminating the need for body section 30. Additionally, in rare instances, the location of the epidural space may be detected by a positive pressure instead of a loss of resistance.

It is also to be understood that the following claims are intended to cover all of the generic and specific features of the invention described herein and all statements of the scope of the invention that as a matter of language might fall therebetween.

What is claimed is:

1. An epidural space locating device for locating an epidural space, the device comprising:
    a body section having a first end and a second end and a longitudinal passageway extending therethrough, the first end of which is coupleable to a luer assembly; and
    a collapsible bellows chamber having one end coupled to the second end of the body section and the other end exposed so as to permit pressure to be exerted thereon by one or more digits of a hand, wherein positive pressure within the bellows chamber maintains the integrity of the shape of the bellows chamber and wherein negative or zero pressure within the bellows chamber facilitates the collapsing of the shape of the bellows chamber thus indicating the locating of the epidural space by a needle that is coupled to the luer assembly as the needle enters the epidural space;
    wherein the loss of pressure within the bellows chamber is sensed by the one or more digits of the hand as the shape of the bellows chamber collapses.

2. The epidural space locating device as claimed in claim 1, including a luer lock coupled to the first end of the body section, the luer lock for air-tightly coupling a needle to the body section.

3. The epidural space locating device as claimed in claim 2, including a needle assembly comprising a needle hub and epidural needle coupled to the luer lock.

4. The epidural space locating device as claimed in claim 1, wherein the bellows chamber includes a neck portion, the neck portion being air-tightly coupled to the second end of the body section, and wherein the neck portion has an air passageway that is inline with the longitudinal passageway extending through the body section.

5. The epidural space locating device as claimed in claim 3, wherein the bellows chamber includes a neck portion, the neck portion being air-tightly coupled to the second end of the body section, and wherein the neck portion has an air passageway that is inline with the passageway of the needle.

6. The epidural space locating device as claimed in claim 4, wherein the bellows chamber and the neck portion are integrally formed and the neck portion and the first end of the body section are threadably coupled:
    whereby the bellows chamber is removeable from the body section by the repeated turning of the neck portion relative to the body section.

7. The epidural space locating device as claimed in claim 1, wherein the body section includes outwardly extending finger grips, the finger grips for providing support of the locating device when pressure is being asserted against the bellow chamber; and
    wherein a squeezing force exerted by and between a thumb of a hand upon a first end of the bellows chamber and other digits of the same hand being engaged against the finger grips facilitates the detection of the negative or zero pressure within the bellows chamber when a needle coupled to the locating device enters the epidural space.

8. The epidural space locating device as claimed in claim 7, wherein the first end of the bellows chamber includes a concave surface for supporting the thumb of the hand, wherein the negative or zero pressure within the bellows chamber is detected by the thumb of the hand as the bellow chamber collapses.

9. The epidural space locating device as claimed in claim 1, wherein the bellows chamber is made of polyethlyene or rubber.

10. A method for detecting the entry of a needle into the epidural space of a patient, the method comprising the steps of:
providing an epidural space locating device comprising a body section having a first end and a second end and a longitudinal passageway extending therethrough, the first end of which is coupleable to a luer assembly; and a collapsible bellows chamber having a first end coupled to the second end of the body section and a second end exposed so as to permit pressure to be exerted thereon by one or more digits of a hand, wherein positive pressure within the bellows chamber maintains the integrity of the shape of the bellows chamber and wherein negative or zero pressure within the bellows chanter facilitates the collapsing of the shape of the bellows chamber thus indicating the locating of the epidural space by a needle that is coupled to the luer assembly;
coupling a luer assembly and epidural needle to said locating device;
inserting the needle into a patient towards the patient's epidural space;
continuing to insert the needle towards the patient's epidural space while applying pressure against the second end of the bellows chamber by a digit of a hand until the shape of the bellows chamber begins to collapse, thereby indicating entrance into the epidural space.

11. The method as claimed in claim 10, including the step of sensing a drop of pressure in the bellows chamber by the thumb of the hand against the second end of the bellows chamber.

12. The method as claimed in claim 10, including the step of inserting the needle into at least the interspinous ligament as the needle is moving towards the epidural space.

13. The method as claimed in claim 11, wherein the bellows chamber includes a neck portion, the method comprising the step of:
air-tightly coupling the neck portion to the body section by threadably screwing the neck portion into one end of the body section;
wherein the neck portion has an air passageway that is inline with the longitudinal passageway extending through the body section.

14. The method as claimed in claim 12, including the step of:
removing the bellows chamber from the body section by the repeated turning of the neck portion relative to the body section.

15. The method as claimed in claim 10, including the steps of:
introducing a solution into the bellows chamber;
inserting the needle into a patient towards the patient's epidural space;
continuing to insert the needle towards the patient's epidural space while applying pressure against the second end of the bellows chamber by a digit of a hand until the shape of the bellows chamber begins to collapse by the solution being introduced into the epidural space, thereby indicating entrance into the epidural space.

16. The method as claimed in claim 15, wherein the solution is introduced into the bellows chamber as the second end of the bellows chamber is pulled in a direction away from the body section.

17. The method as claimed in claim 10, wherein the body section includes outwardly extending finger grips for providing support and guidance of the locating device when pressure is being asserted against the bellow chamber, wherein the method comprises the steps of:
providing a squeezing force by and between a thumb of a hand upon the first end of the bellows chamber and other digits of the same hand being engaged against the finger grips;
whereby there is a facilitation of the detection of the negative or zero pressure within the bellows chamber when a needle coupled to the locating device enters the epidural space.

18. A method for deflecting a patient's dura for preventing dural puncture, the method comprising the steps of:
providing an epidural space locating device comprising a body section having a first end and a second end and a longitudinal passageway extending therethrough, the first end of which is coupleable to a luer assembly; and a collapsible bellows chamber having a first end coupled to the second end of the body section and a second end exposed so as to permit pressure to be exerted thereon by one or more digits of a hand, wherein positive pressure within the bellows chamber maintains the integrity of the shape of the bellows chamber and wherein negative or zero pressure within the bellows chamber facilitates the collapsing of the shape of the bellows chamber thus indicating the locating of the epidural space by a needle that is coupled to the luer assembly;
coupling a luer assembly and epidural needle to said locating device;
inserting the needle into a patient towards the patient's epidural space;
continuing to insert the needle towards the patient's epidural space while applying pressure against the second end of the bellows chamber by a digit of a hand until the shape of the bellows chamber begins to collapse, thereby deflecting a patient's dura for preventing dural puncture.

19. The method as claimed in claim 18, including the step of sensing a drop of pressure in the bellows chamber by a thumb of the hand against the second end of the bellows chamber.

20. The method as claimed in claim 18, including the step of inserting the needle into at least the interspinous ligament as the needle is moving towards the epidural space.

21. The method as claimed in claim 18, including the steps of:
introducing a solution into the bellows chamber;
inserting the needle into a patient towards the patient's epidural space;
continuing to insert the needle towards the patient's epidural space while applying pressure against the second end of the bellows chamber by a digit of a hand until the shape of the bellows chamber begins to collapse by the solution being introduced into the epidural space, thereby indicating entrance into the epidural space.

22. The method as claimed in claim 22, wherein the solution is introduced into the bellows chamber as the second end of the bellows chamber is pulled in a direction away from the body section.

23. The method as claimed in claim 18, wherein the body section includes outwardly extending finger grips for providing support and guidance of the locating device when pressure is being asserted against the bellow chamber, wherein the method comprises the steps of:

providing a squeezing force by and between a thumb of a hand upon the first end of the bellows chamber and other digits of the same hand being engaged against the finger grips;

whereby there is a facilitation of the detection of the negative or zero pressure within the bellows chamber when a needle coupled to the locating device enters the epidural space.

* * * * *

UNITED STATES PATENT AND TRADEMARK OFFICE
CERTIFICATE OF CORRECTION

PATENT NO.     : 6,773,417 B2
DATED          : August 10, 2004
INVENTOR(S)    : James F. Fitzgibbons and Christopher S. Young It is certified that error appears in the above-identified patent and that said Letters Patent is hereby corrected as shown below:

Column 5,
Line 48, delete the reference number "36" and replace it with the reference number -- 33 --

Column 6,
Line 6, delete the reference number "36" and replace it with the reference number -- 33 --

Column 11,
Line 3, delete the number "22" between the words "claim" and "wherein" and replace it with the number -- 21 --

Signed and Sealed this

Twenty-first Day of September, 2004

JON W. DUDAS
*Director of the United States Patent and Trademark Office*